United States Patent
Fujisawa et al.

(10) Patent No.: US 8,501,210 B2
(45) Date of Patent: *Aug. 6, 2013

(54) GEL COMPOSITION AND PACK COSMETIC USING THE SAME

(75) Inventors: Masaaki Fujisawa, Yokohama (JP); Keiko Tanaka, Yokohama (JP); Keiichi Oyama, Yokohama (JP)

(73) Assignee: The Nisshin Oillio Group, Ltd (JP)

( * ) Notice: Subject to any disclaimer, the term of this patent is extended or adjusted under 35 U.S.C. 154(b) by 372 days.

This patent is subject to a terminal disclaimer.

(21) Appl. No.: 12/281,400

(22) PCT Filed: Mar. 6, 2007

(86) PCT No.: PCT/JP2007/054249
§ 371 (c)(1),
(2), (4) Date: Oct. 9, 2008

(87) PCT Pub. No.: WO2007/105526
PCT Pub. Date: Sep. 20, 2007

(65) Prior Publication Data
US 2009/0130039 A1    May 21, 2009

(30) Foreign Application Priority Data
Mar. 10, 2006 (JP) .................... 2006-065639

(51) Int. Cl.
*A61K 31/00* (2006.01)
*A61K 9/00* (2006.01)
*A01N 45/00* (2006.01)
*A01N 25/00* (2006.01)

(52) U.S. Cl.
USPC .............................. 424/418; 424/461; 514/54

(58) Field of Classification Search
USPC ...................... 514/54; 424/418, 461
See application file for complete search history.

(56) References Cited

U.S. PATENT DOCUMENTS

| 4,074,043 A | | 2/1978 | Jones et al. |
| 4,895,938 A | | 1/1990 | Teraoka et al. |
| 5,403,599 A | * | 4/1995 | Whistler .......................... 426/48 |
| 6,056,950 A | * | 5/2000 | Saettone et al. ............ 424/78.04 |

FOREIGN PATENT DOCUMENTS

| JP | 64-022901 | | 1/1989 |
| JP | 10-167951 | | 6/1998 |
| JP | 2003-082003 | | 3/2003 |
| JP | 2004-091360 | | 3/2004 |
| JP | 2004-168725 | | 6/2004 |
| JP | 2005-060237 | | 3/2005 |
| JP | 2006-008615 | | 1/2006 |
| JP | 2006-008920 | | 1/2006 |
| JP | 2006008615 A | * | 1/2006 |
| JP | 2006-289711 | | 10/2006 |
| KR | 20030018151 A | * | 3/2003 |

OTHER PUBLICATIONS

NTS Inc.; Gel Handbook; Nov. 28, 1997; Japan.

* cited by examiner

*Primary Examiner* — Fereydoun G Sajjadi
*Assistant Examiner* — Courtney Brown
(74) *Attorney, Agent, or Firm* — Clark Hill PLC

(57) ABSTRACT

The present invention has an object to provide a gel composition which has an excellent skin whitening effect and shows high storage stability even when ascorbic acid, a salt of ascorbic acid, an ascorbic acid derivative, and a salt of an ascorbic acid derivative is blended, and to provide a pack cosmetic using the gel composition. The gel composition, which comprises the following components (A)-(D): (A) a tamarind seed polysaccharide; (B) a polyhydric alcohol; (C) at least one or more of ascorbic acid, a salt of ascorbic acid, an ascorbic acid derivative, and a salt of an ascorbic acid derivative; and (D) water.

9 Claims, No Drawings

GEL COMPOSITION AND PACK COSMETIC USING THE SAME

RELATED/PRIORITY APPLICATION

This application is a National Phase filing regarding International Application No. PCT/JP2007/054249, filed on Mar. 6, 2007, which relies upon Japanese Application No. 2006-065639, filed on Mar. 10, 2006 for priority.

TECHNICAL FIELD

The present invention relates to a gel composition containing at least one or more of ascorbic acid, a salt of ascorbic acid, an ascorbic acid derivative, and a salt of an ascorbic acid derivative. It also relates to a pack cosmetic using the gel composition.

BACKGROUND ART

Pack cosmetics have been widely used in cosmetic products and quasi-drugs from old times. The use thereof is not only for faces but also widely spreads over topical use for necks, shoulders, arms, and legs as well as systemic use. The primary object to use pack cosmetics is to cover skins with a coating for a certain period of time, thereby imposing the moisture retentivity on skins and causing effective penetration through skins of drug components compounded in the coating. An available pack cosmetic is polyvinyl alcohol. The polyvinyl alcohol has an excellent coating formability and can achieve such the object. Accordingly, it has been compounded in many pack cosmetics previously (Patent Document 1). The polyvinyl alcohol, however, increasingly decomposes over time and lowers the pH of an aqueous solution as a problem.

Of pack cosmetics, packs of the sheet type in particular include a hydrous gelling agent developed as the base for poultices in the field of medicines. The hydrous gelling agent includes a water-soluble polymer capable of retaining water and specifically uses an acrylic acid-based polymer in general. If the carboxyvinyl polymer is used in formulae containing various salts, the thickening effect thereof may lower as a problem (Patent Document 2).

In recent years, ascorbic acid and derivatives thereof, and salts thereof (hereinafter referred to as ascorbic acid and analogues generally) are added as a whitening agent to impose the whitening effect on various cosmetics. The ascorbic acid and analogues are excellent in the whitening effect and stable in aqueous solution at a pH of about 6-9. In contrast, they are hardly stable in aqueous solution at a pH lower than 6 and cause variations in color and odor and occurrences of aggregations overtime as a problem. From such the consideration, it is difficult, with regard to the stability of the ascorbic acid and analogues, to compound ascorbic acid and derivatives thereof in the above-listed pack cosmetics containing polyvinyl alcohol as a problem. A method is developed to solve the problem, which comprises using a 2-O-D-glucopyranosyl-L-ascorbic acid derivative as a whitening effect component and compounding urea therewith (Reference 3).

Patent Document 1: JP 10-167951A
Patent Document 2: JP 2004-91360A
Patent Document 3: JP 2004-91360A

DISCLOSURE OF THE INVENTION

Problems to be Solved by the Invention

The method comprises using no ascorbic acid and analogues other than a specific ascorbic acid derivative and always compounding urea. Accordingly, it has restrictions on formulae and uses as a problem.

Also in the packs of the sheet type containing an acrylic acid-based polymer such as the carboxyvinyl polymer, it is difficult, with regard to the thickening effect, to compound a salt of ascorbic acid and a salt of an ascorbic acid derivative as a problem.

The present invention has an object to provide a gel composition which has an excellent skin whitening effect and shows high storage stability even when ascorbic acid, a salt of ascorbic acid, an ascorbic acid derivative, and a salt of an ascorbic acid derivative is blended, and to provide a pack cosmetic using the gel composition.

Means to Solve the Problems

The inventors et al. have eagerly studied for the purpose of solving the above problems and consequently found that compounding a tamarind seed polysaccharide and a polyhydric alcohol makes it possible to obtain a gel composition and a pack cosmetic which have an excellent skin whitening effect and shows high storage stability even when ascorbic acid, a salt of ascorbic acid, an ascorbic acid derivative, and a salt of an ascorbic acid derivative is blended. Namely, the present invention provides a gel composition, which comprises the following components (A)-(D): (A) a tamarind seed polysaccharide; (B) a polyhydric alcohol; (C) at least one or more of ascorbic acid, a salt of ascorbic acid, an ascorbic acid derivative, and a salt of an ascorbic acid derivative; and (D) water.

Effects of the Invention

As described above, in accordance with the present invention, a high-stability gel composition and pack cosmetic imposed with the whitening effect and the moisture retentivity can be obtained.

THE BEST MODE FOR CARRYING OUT THE INVENTION

The gel composition of the present invention composes the gel base material of the components (A) and (B). The gel base material may include other gel base materials than the components (A) and (B). It is preferable, though, not to blend the polyvinyl alcohol and acrylic acid-based polymers (such as the carboxyvinyl polymer) as gel base material because they exert an influence on the stability of ascorbic acid and analogues. More preferably, the gel composition of the present invention comprises the gel base material containing the components (A) and (B) (except the polyvinyl alcohol and acrylic acid-based polymers), and also comprises the components (C) and (D).

In the gel composition of the present invention, preferably, the component (A) is a tamarind seed polysaccharide including not less than 90% by mass of dietary fiber, not more than 1% by mass of protein, and not more than 1% by mass of ash. Preferably, the content of the component (A) is 1-20% by mass, the content of the component (B) is 3-50% by mass, the content of the component (C) is 0.01-10% by mass, and the content of the component (D) is 20-95.99% by mass.

The present invention also provides a pack cosmetic using the gel composition, which may comprise a support.

The component (A) used in the gel composition of the present invention is a tamarind seed polysaccharide. The tamarind seed polysaccharide is a polysaccharide extracted from the seeds of a perennial leguminous plant, Tamarindous Indica, grown over Southeast Asia such as India and Burma.

In general, it can be dissolved in water completely when heated up to 80° C. or higher. An aqueous solution thereof has almost Newtonian viscosity and is excellent in resistance to acids, heat, and salts and thus widely used in the field of foods in general. The tamarind seed polysaccharide is known to form an aqueous gel in the coexistence of saccharides such as sugar and millet jelly, or ethanol. The commodity products using the function thereof include almost nothing other than jelly-like foods, and moisture retainers for cosmetics.

The tamarind seed polysaccharide may be one of commercially available products. Among those, in particular, the use of a purified tamarind seed polysaccharide from which insoluble components are removed or reduced, specifically a tamarind seed polysaccharide adjusted to include not less than 90% by mass of dietary fiber, not more than 1% by mass of protein, and not more than 1% by mass of ash is preferable with regard to the stabilization of ascorbic acid and analogues. Examples of such the purified tamarind seed polysaccharide may include an item: Nom Coat EP-2 available from Nisshin Oillio Group, Ltd.

Methods of analyzing the content of dietary fiber in the tamarind seed polysaccharide may include an enzyme-gravimetric method (Prosky-AOAC method). Methods of analyzing the content of protein in the tamarind seed polysaccharide may include a semi-micro kjedahl method, which is a nitrogen determination method described in the Japanese Standards for Food Additives. Specifically, the quantity of nitrogen (N) in 0.5 g of a specimen is measured and multiplied by 5.7 to obtain the content of protein (1 ml of 0.01 N sulfuric acid=0.1401 mgN). Methods of analyzing the content of ash in the tamarind seed polysaccharide may include the following method described in the Japanese Standards for Food Additives. Namely, the method comprises collecting 1 g of a specimen, gently heating the specimen for carbonization, then intensely heating it at 500-600° C. until the carbonized product can not be observed and reaches to a constant weight, and measuring the amount of the residue to obtain the content of ash.

The content of the component (A) in the gel composition of the present invention is preferably 1-20% by mass, more preferably 2-15% by mass, and most preferably 3-10% by mass. The content of the component (A) falling within this range leads to production of a gel with higher stability and better feeling in use.

The component (B) for use in present invention is described next. The component (B) used in the gel composition of the present invention is a polyhydric alcohol. The polyhydric alcohol may be one of commercially available products. Specific examples of the polyhydric alcohol include glycerin, diglycerin, triglycerin, polyglycerin, pentaerythritol, dipentaerythritol, xylitol, ethylene glycol, diethylene glycol, polyethylene glycol, propylene glycol, dipropylene glycol, tripropylene glycol, polyethylene glycol, trimethylene glycol, 1,2-butylene glycol, 1,3-butylene glycol, hexylene glycol, 1,2-pentandiol, 1,2-hexandiol, and erythritol, of which one or two or more may be used. Among those, the use of 2- to 5-valent polyhydric alcohols, in particular, glycerin, propylene glycol, or 1,3-butylene glycol is preferable with regard to the feeling in use of the gel. The joint use of two or three selected from glycerin, propylene glycol, and 1,3-butylene glycol is more preferable with regard to the feeling in use of the gel and feeling in moisture retention.

The content of the component (B) in the gel composition of the present invention is preferably 3-50% by mass, more preferably 10-45% by mass, and most preferably 20-40% by mass. The content of the component (B) falling within this range leads to production of a gel with higher stability and better feeling in use.

The component (C) for use in the present invention is described next. The component (C) used in the gel composition of the present invention includes one or two or more selected from ascorbic acid, salts of ascorbic acid, ascorbic acid derivatives, and salts of ascorbic acid derivatives. The ascorbic acid, salts of ascorbic acid, ascorbic acid derivatives, and salts of ascorbic acid derivatives are not limited in particular if they are used usually in cosmetics and medicines, and may be commercially available products. Specifically, examples of the ascorbic acid may include L-ascorbic acid. The salts of ascorbic acid may include sodium salts, potassium salts, magnesium salts, calcium salts, barium salts, ammonium salts, monoethanolamine salts, diethanolamine salts, triethanolamine salts, monoisopropanolamine salts, and triisopropanolamine salts. The ascorbic acid derivatives may include L-ascorbic acid monoesters such as L-ascorbic acid glucoside, L-ascorbic acid 2-phosphate, L-ascorbic acid 3-phosphate, L-ascorbic acid 6-phosphate, L-ascorbic acid 2-polyphosphate, and L-ascorbic acid 2-sulfate; L-ascorbic acid monoalkylesters such as L-ascorbic acid 2-palmitate, L-ascorbic acid 6-palmitate, L-ascorbic acid 2-stearate, and L-ascorbic acid 6-stearate; L-ascorbic acid dialkylesters such as L-ascorbic acid 2,6-dibutyl ester, and L-ascorbic acid 2,6-dipalmitate; L-ascorbic acid trialkylesters such as L-ascorbic acid tristearate, L-ascorbic acid trioleate, and L-ascorbic acid tripalmitate; L-ascorbic acid triesters such as L-ascorbic acid triphosphate; and L-ascorbic acid tetraalkylesters such as L-ascorbyl tetraisopalmitate. The salts of ascorbic acid derivatives may include sodium salts, potassium salts, magnesium salts, calcium salts, barium salts, ammonium salts, monoethanolamine salts, diethanolamine salts, triethanolamine salts, monoisopropanolamine salts, and triisopropanolamine salts. Among those, the use of magnesium L-ascorbic acid 2-phosphate, or sodium L-ascorbic acid 2-phosphate is preferable with respect to the whitening effect.

The content of the component (C) in the gel composition of the present invention is preferably 0.01-10% by mass, more preferably 0.1-5% by mass, and most preferably 1-4% by mass. The content of the component (C) falling within this range provides the gel composition with higher stability and exerts the effect in relation to the compounding amount, which has an advantage in costs.

The component (D) for use in the present invention is described next. The component (D) used in the gel composition of the present invention includes water, which is not limited in particular if the water can be used in cosmetics. Specifically, available examples include tap water, ion-exchanged water, membrane-treated water, distilled water, super-pure water, fruit water, and deep ocean water.

The content of the component (D) in the gel composition of the present invention is preferably 20-95.99% by mass, more preferably 35-87.9% by mass, and most preferably 46-76% by mass.

The gel composition of the present invention preferably has a pH of 6-9, more preferably a pH of 7-9, and most preferably a pH of 7.5-8.5.

The gel composition of the present invention may be compounded with various components used in general cosmetics other than the above-described components (A), (B), (C) and (D), if required, without impairment of the effect of the invention. Such components, which differ depending on the use and dosage form of cosmetics, may include oily components, aqueous components, anionic surfactants, cationic surfactants, amphoteric surfactants, lipophilic surfactants, hydrophilic surfactants, natural surfactants, moisture retainers, thickeners, antiseptics, powdery components, pigments, pH adjusters, antioxidants, UV absorbers, perfumes, coloring matters, and chelating agents.

The oily components may include hydrocarbons such as fluid paraffin, heavy fluid isoparaffin, solid paraffin, α-olefin oligomer, squalane, vaseline, polyisobutylene, polybutene, montan wax, ceresin wax, micro-crystalline wax, polyethylene wax, and Fisher-Tropsh wax; oils and fats such as olive oil, castor oil, jojoba oil, mink oil, and Macadamia nut oil; waxes such as beeswax, candelilla wax, spemaceti wax, candelilla wax, and carnauba wax; esters such as vegetable wax, cetyl 2-ethyl hexanoate, cetyl isooctanoate, isopropyl myristate, isopropyl palmitate, octyldodecyl myristate, polyglyceryl diisostearate, polyglyceryl triisostearate, diglyceryl triisostearate, polyglyceryl tetraisostearate, diglyceryl tetraisostearate, trioctanoin, diisostearylmalate, neopentyl glycol dioctanoate, propylene glycol didecanoate, cholesterol fatty acid ester, isopropyl myristate, glyceryl monostearate, glycerin fatty acid ester eicosanoic diacid condensation products, dextrin palmitate, dextrin myristate, and dextrin fatty acid esters; fatty acids such as stearic acid, lauric acid, myristic acid, behenic acid, isostearylic acid, and oleic acid; high grade alcohols such as stearyl alcohol, cetyl alcohol, lauroyl alcohol, oleyl alcohol, isostearyl alcohol, behenyl alcohol, stearyl alcohol, octyl dodecanol, and isohexadecyl alcohol; silicon analogues such as dimethyl polysiloxane with low degrees of polymerization, dimethyl polysiloxane with high degrees of polymerization, methylphenyl polysiloxane, decamethyl cyclopenta siloxane, octamethyl cyclotetra siloxane, polyether-modified polysiloxane, polyoxyalkylene-alkylmethyl polysiloxane-methyl polysiloxane copolymers, and alkoxy-modified polysiloxane; fluorine-based oils such as perfluorodecane, perfluorooctane, and perfluoro polyether; N-acyl glutamates such as stearoyl glutamate; amino acid-based ester oils such as di(cholesteryl or phytosterol/behenyl/octyldodecyl) N-lauroyl-L-glutamate; and lanolin derivatives such as lanolin, liquid lanolin, lanolin acetate, liquid lanolin acetate, lanolin fatty acid isopropyl, and lanolin alcohol. The above oil components may be used solely or in combination of two or more.

The aqueous components may include low grade alcohols such as ethyl alcohol, and butyl alcohol; and animal and plant extracts such as nettle leaf extract, eleutherococcus senticosus extract, phellodendri cortex extract, coffee extract, white birch extract, mentha piperita extract, thyme extract, tea extract, witch hazel extract, rabdosia japonica extract, fussilago farfara extract, grape vine leaf extract, hop extract, marronnier extract, melissa extract, acerola extract, rose multiflora thunberg extract, kiwifruit extract, arnica extract, sutellariae radix extract, coptis japonica extract, lamium album var. barbatum lamium extract, typha latifolia extract, matricaria chamomilla extract, artemisia capillaris extract, licoris extract, gardenia jasminoidos extract, sasa veitchii extract, gentiana extract, tea extract, comfrey extract, perilla frutescens extract, lithospermum erythrorhizon extract, Japanese linden extract, filipendula multijuga maxim extract, paeonia lactiflora extract, lonicera japonice extract, common sage extract, ground ivy extract, black elder extract, yarrow extract, swertia japonica extract, mori crotex extract, calenduta officinails extract, eriobotrya japonica extract, peach leaf extract, centaurea syanus extract, saxifrage stolonifera extract, artenisia princeps extract, lettuce extract, chamomile extract, and sanguisorba officinails, of which one or two or more may be used.

The anionic surfactants may include fatty acid soaps such as ground for soaps, sodium laurate, and sodium palmitate; high grade alkylsulfate salts such as sodium lauryl sulfate, and potassium lauryl sulfate; alkylether sulfate salts such as polyoxyethylene (POE)-triethanolamine lauryl sulfate, and POE-sodium lauryl sulfate; N-acylsarcosinate such as sodium lauroyl sarcosinate; high grade fatty acid amidosulfonate salts such as sodium N-myristoyl-N-methyl taurine, sodium palm oil fatty acid methyl tauride, and sodium lauryl methyl tauride; phosphate salts such as POE-sodium oleylether phosphate, and POE-stearylether phosphate; sulfosuccinate salts such as sodium di-2-ethylhexyl sulfosuccinate, sodiummonolauroyl monoethanol amide polyoxyethylene sulfosuccinate, and sodium lauryl polypropylene glycol sulfosuccinate; alkylbenzen sulfonate salts such as sodium linear dodecyl benzen sulfonate, triethanol amine linear dodecyl benzen sulfonate, and linear dodecyl benzen sulfonate; N-acylglutamate salts such as monosodium N-lauroyl glutamate, disodium N-stearoyl glutamate, and monosodium N-myristoyl-L-glutamate; high grade fatty acid ester sulfate salts such as sodium cured palm oil fatty acid glycerin sulfate; sulfated oils such as turkey red oil; and others such as POE-alkylether carboxylate, POE-alkylallylether carboxylate salts, α-olefin sulfonate salts, high grade fatty acid ester sulfonate salts, secondary alcohol sulfate salts, high grade fatty acid alkylol amide sulfate salts, sodium lauroyl monoethanol amide succinate, ditriethanol amine N-palmitoyl asparaginate, and sodium casein. The above anionic surfactants may be used solely or in combination of two or more.

The cationic surfactants may include alkyltrimethyl ammonium salts such as stearyl trimethyl ammonium chloride, and lauryl trimethyl ammonium chloride; dialkyldimethyl ammonium salts such as distearyl dimethyl ammonium chloride; alkylpyridinium salts such as poly(N,N'-dimethyl-3,5-methylene piperidinium) chloride, and cetyl pyridinium chloride; and others such as alkyl quaternary ammonium salts, alkyl dimethyl benzyl ammonium salts, alkyl iso-quinolinium salts, dialkyl morihonium salts, POE-alkylamine, alkylamine salts, polyamine fatty acid derivatives, amyl alcohol fatty acid derivatives, benzalkonium chloride, and benzethonium chloride. The cationic surfactants may be used solely or in combination of two or more.

The amphoteric surfactants may include imidazolin-based amphoteric surfactants such as sodium 2-undecyl-N,N,N-(hydroxyethyl carboxymethyl)-2-imidazolin, and 2-cocoyl-2-imidazolinium hydroxide-1-carboxy ethyloxy disodium salts; and betaine-based surfactants such as 2-heptadecyl-N-carboxymethyl-N-hydroxyethyl imidazolinium betaine, lauryl dimethyl amino acetate betaine, alkylbetaine, amidobetaine, and sulfobetaine. The amphoteric surfactants may be used solely or in combination of two or more.

The lipophilic surfactants may include sorbitane fatty acid esters such as sorbitane monooleate, sorbitane monoisostearate, sorbitane monolaurate, sorbitane monopalmitate, sorbitane monostearate, sorbitane sesquioleate, sorbitane trioleate, penta-2-ethylhexylate diglycerol sorbitane, and tetra-2-ethylhexylate diglycerol sorbitane; sucrose fatty acid esters; glycerin fatty acids such as glycerin mono cottonseed oil fatty acid, glycerin monoerucate, glycerin sesquioleate, glycerin monostearate, glycerin α,α'-oleate pyroglutamate, and glycerin monostearate; polyglycerin fatty acid esters such as diglyceryl monoisostearate, and diglyceryl diisostearate; propylene glycol fatty acid esters such as propylene glycol monostearate; and others such as cured castor bean oil derivatives, and glycerin alkylether. The lipophilic surfactants may be used solely or in combination of two or more.

The hydrophilic surfactants may include POE-sorbitan fatty acid esters such as POE-sorbitan monooleate, POE-sorbitan monostearate, POE-sorbitan monoolate, and POE-sorbitan tetraoleate; POE-sorbit fatty acid esters such as POE-sorbit monoraulate, POE-sorbit monooleate, POE-sorbit pentaoleate and POE-sorbit monostearate; POE-glycerin fatty acid esters such as POE-glycerin monostearate, POE-glycerin monoisostearate, and POE-glycerin triisostearate; POE-fatty acid esters such as POE-monooleate, POE-distearate, POE-monodioleate, and ethylene glycol distearate; POE-alkylethers such as POE-lauryl ether, POE-oleyl ether, POE-stearyl ether, POE-behenyl ether, POE-2-octyldodecyl ether, and POE-cholestanol ether; pluronic analogues such as pluronic; POE/POP-alkyl ethers such as POE/POP-cetyl ether, POE/POP-2-decyl tetradecyl ether, POE/POP-monobutyl ether, POE/POP-hydrogenated lanolin, and POE/POP-glycerin ether; tetra POE/tetra POP-ethylene diamine polymers such as tetronic; POE-castor bean oil/cured castor bean oil derivatives such as POE-castor bean oil, POE-cured castor bean oil, POE-cured castor bean oil monoisostearate, POE-cured castor bean oil triisostearate, POE-cured castor bean oil monopyroglutamate monoisostearate diester, and POE-cured castor bean oil maleate; POE-beeswax/lanolin derivatives such as POE-sorbit beeswax; alkanolamides such as palm oil fatty acid diethanolamide, laurate monoethanol amide, and fatty acid isopropanol amide; and others such as POE-propylene glycol fatty acid esters, POE-alkyl amine, POE-fatty acid amide, sucrose fatty acid esters, POE-nonylphenyl formaldehyde polymers, alkyl ethoxy dimethyl amine oxide, and trioleyl phosphate. The hydrophilic surfactants may be used solely or in combination of two or more.

The natural surfactants may include lecithins such as soy bean phospholipid, hydrogenated soy bean phospholipid, yolk phospholipid, and hydrogenated yolk phospholipid; and others such as soy bean saponin. The natural surfactants may be used solely or in combination of two or more.

The moisture retainers may include condroitin sulfuric acid, hyaluronic acid, mucoitin sulfuric acid, caronic acid, aterocollagen, cholesteryl-12-hydroxystearate, sodium lactate, urea, bile acid salts, dl-pyrrolidone carbonate salts, short-chain soluble collagen, rosa roxburghii extract, yarrow extract, and melilot extract. The moisture retainers may be used solely or in combination of two or more.

The thickeners may include gum arabic, carrageenan, gum karaya, tragacanth gum, carob gum, quins seed (mermelo), casein, dextrin, gelatin, sodium pectinate, sodium alginate, methyl cellulose, ethyl cellulose, CMC, hydroxyethyl cellulose, hydroxypropyl cellulose, locust bean gum, guar gum, xanthan gum, aluminum magnesium silicate, bentonite, hectorite, quaternary ammonium salt type cation-modified bentonite, quaternary ammonium salt type cation-modified hectorite, and decaglycerin fatty acid ester eicosanoic diacid condensation products. The thickeners may be used solely or in combination of two or more.

The antiseptics may include ethylparaben, and butylparaben. The antiseptics may be used solely or in combination of two or more.

The powdery components may include inorganic powders such as talc, kaoling, mica, sericite, muscovite, phlogopite, synthetic mica, lepidolite, biotite, trilithionite, vermiculite, magnesium carbonate, calcium carbonate, aluminum silicate, barium silicate, calcium silicate, magnesium silicate, strontium silicate, metal tungstate, magnesium, silica, zeolite, barium sulfate, calcined calcium sulfate, (dorling kindersley), calcium phosphate, fluoroapatite, hydroxyapatite, ceramic powder, metal soap (zinc myristate, calcium palmitate, aluminum stearate), and boron nitride; and organic powders such as polyamide resin power (nylon powder), polyethylene powder, methyl polymethacrylate powder, polystyrene powder, styrene-acrylic acid copolymer resin powder, benzoguanamine resin powder, polytetrafluoroethylene powder, and cellulose powder. The powdery components may be used solely or in combination of two or more.

The pigments may include inorganic white pigments such as titanium dioxide and zinc oxide (including particulate titanium dioxide and zinc oxide used as UV scattering agents, of which surfaces may be coated with fatty acid soaps such as aluminum stearate, and zinc palmitate, fatty acids such as stearic acid, myristic acid, and palmitic acid, and fatty acid esters such as dextrin palmitate to form surface-coated inorganic white pigments); inorganic red pigments such as iron oxide (bengala), and iron titanate; inorganic brown pigments such as γ-iron oxide; inorganic yellow pigments such as yellow iron oxide, and yellow Chinese loess; inorganic black pigments such as black iron oxide, carbon black, and low-order titanium oxide; inorganic violet pigments such as mango violet, and cobalt violet; inorganic green pigments such as chromium oxide, chromium hydroxide, and cobalt titanate; inorganic blue pigments such as sea blue, and prussinan blue; pearl pigments such as titanium oxide-coated mica, titanium oxide-coated bismuth oxycholoride, titanium oxide-coated talc, colored titanium oxide-coated mica, bismuth oxycholoride, and dew pearl; metal power pigments such as aluminum powder, and copper powder; organic pigments such as Red No. 201, Red No. 202, Red No. 204, Red No. 205, Red No. 220, Red No. 226, Red No. 228, Red No. 405, Orange No. 203, Orange No. 204, Yellow No. 205, Yellow No. 401, and Blue No. 404; and organic pigments, for example, zirconium, and barium or aluminum lake such as Red No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3, and Blue No. 1. The pigments may be used solely or in combination of two or more.

The pH adjusters and chelating agents may include edetic acid, disodium edetate, citric acid, sodium citrate, sodium hydroxide, potassium hydroxide, triethanol amine, and hydroxyethane diphosphonate. The pH adjusters and chelating agents may be used solely or in combination of two or more.

The antioxidants may include tocopherols, derivatives thereof, salts thereof, dibutylhydroxy toluene, butylhydroxy anisole, and gallates. The antioxidants may be used solely or in combination of two or more.

The UV absorbers may include benzoic acid-based UV absorbers such as paramino benzoic acid (hereinafter abbreviated as PABA), PABA monoglycerin ester, N,N-dipropoxy PABA ethyl ester, N,N-diethoxy PABA ethyl ester, N,N-dimethyl PABA ethyl ester, N,N-dimethyl PABA butyl ester, and N,N-dimethyl PABA ethyl ester; anthranilic acid-based UV absorbers such as homomethyl-N-acetylanthranilate; salicylic acid-based UV absorbers such as amyl salicylate, menthyl salicylate, homomethyl salicylate, octyl salicylate, phenyl salicylate, benzyl salicylate, p-isopropanol phenyl salicylate; cinnamic acid-based UV absorbers such as octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, octyl-p-methoxy cinnamate (2-ethylhexyl-p-methoxy cinnamate), 2-ethoxyethyl-p-methoxy cinnamate, cyclohexyl-p-methoxy cinnamate, ethyl-α-cyano-β-phenyl cinnamate, 2-ethylhexyl-α-cyano-β-phenyl cinnamate, and glyceryl mono-2-ethylhexanoyl-diparamethoxy cinnamate; benzophenone-based UV absorbers such as 2,4-dihydroxy benzophenone, 2,2'-dihydroxy-4-methoxy benzophenone, 2,2'-dihydroxy-4,4'-dimethoxy benzophenone, 2,2',4,4'-tetrahydroxy benzophenone, 2-hydroxy-4-methoxy benzophenone, 2-hydroxy-4-methoxy-4'-methyl benzophenone, 2-hydroxy-4-methoxy-benzophenone-5-sulfonate salt, 4-phenyl benzophenone, 2-ethylhexyl-4'-phenyl-benzophenone-2-carboxylate, 2-hydroxy-4-n-octoxy benzophenone, and 4-hydroxy-3-carboxy benzophenone; and others such as 3-(4'-methylbenzyliden)-d,l-camphor, 3-benzyliden-d,l-camphor, urocanic acid, urocanate ethyl esters, 2-phenyl-5-methyl benzoxazol, 2,2'-hydroxy-5-methylphenyl benzotriazol, 2-(2'-hydroxy-5'-t-octylphenyl)benzotriazol, 2-(2'-hydroxy-5'-methylphenyl)benzotriazol, dibenzalazine, dianisoyl methane, 4-methoxy-4'-t-butyl dibenzoyl methane, 5-(3,3-dimethyl-2-norbornyliden)-3-pentane-2-on, and 2,4,6-trianilino-p-(carbo-2'-ethylhexyl-1'-oxy) 1,3,5-triazine, and 4-tert-butyl-4'-methoxy dibenzoyl methane. The UV absorbers may be used solely or in combination of two or more.

The perfumes may include α-amylcinnamaldehyde, methyl anthronilate, isoeugenol, γ-undecalactone, ethyl valinine, eugenol, coumarin, cinnamyl alcohol, cinnamaldehyde, methyl cinnamate, ethyl cinnamate, geraniol, geranyl acetate, cytronellyl acetate, cinnamyl acetate, terpinyl acetate, phenylethyl acetate, butyl acetate, isoamyl acetate, 1-menthyl acetate, linalyl acetate, methyl salicylate, citronellol, citronellal, decylaldehyde, γ-nonalacton, valinine, paramethyl acetophenone, hydroxypropyl cellulose, piperonal, phenyl-ethyl alcohol, ethylphenyl acetate, benzyl alcohol, methyphe-nyl polysiloxane, 1-menthole, ionone, linanol, citral, borneol, terpineol, nerolin, diphenyl oxide, acinic aldehyde, dl-camphre, terebic oil, eucalyptus oil, nutmeg oil, ceder leaf oil, musk, ambergris, lavender oil, thymol, and mixtures thereof. The perfumes may be used solely or in combination of two or more.

The coloring matters may include chlorophyll, and β-carotene. The coloring may be used solely or in combination of two or more.

The following description is given to a method of producing gel compositions of the present invention. The method of producing gel compositions of the present invention is not limited particularly. Preferably, it may comprise keeping a temperature of 60° C. or lower for subsequent processes after addition of low-thermal stability ascorbic acids. A specific example of the method of producing gel compositions is shown below. The tamarind seed polysaccharide may be mixed in a powdery form with the components (B), (C). Preferably, after dissolved in the component (D) to produce an aqueous solution, the other components such as (B), (C) are mixed therein. The other components than the component (C), that is, the components (A), (B), (D) and other water-soluble components are supplied into a stirring vessel and mixed at 20-40° C., followed by heating while stirring with a propeller or the like. After the temperature reaches 75-85° C., the mixture is stirred for 30-120 minutes at that temperature. If an oil component is added, it is added after that, followed by propeller stirring for 30 minutes at 80° C. Next, the temperature is adjusted at 45-55° C. and the component (C) is added, followed by additional stirring for 10-20 minutes. The resultant solution is cooled at 5-25° C. for 6-48 hours for gelation to obtain a gel component.

The following description is given to pack cosmetics of the present invention. The pack cosmetics of the present invention use the above-described gel components as pack cosmetics. A gel component may be used as pack cosmetics as it is though it may be used in a state applied on or attached to a support. The types of pack cosmetics of the present invention may include a peel-off type, a wipe-out type, a wash-out type, and a sheet type. The pack cosmetics of the peel-off type may be configured in the forms of jelly, paste and powder. The pack cosmetics of the wipe-out type and the wash-out type may be configured in the forms of emulsion, mud, jelly, and foam. The pack cosmetics of the sheet type may include a nonwoven gel type, a nonwoven impregnated type, and a gel sheet type. Among those, the pack cosmetics of the sheet type are particularly preferable from the viewpoint of the excellent feeling in use. The pack cosmetics of the present invention are available as cosmetic products and quasi-drugs for the purpose of removing oils and contaminants such as sebum on application to cuticles and imposing the moisture retaining effect.

The following description is given to support-equipped pack cosmetics of the present invention. The support-equipped pack cosmetics are such cosmetics that include the gel composition applied on or attached to a support. Available raw materials of the support may include nonwoven such as rayon, cotton, acrylic, nylon, polypropylene, cupro, polylactate, polyester, and polyethylene. Shapes of the support may include various forms in accordance with the use, such as rectangle, square, diamond, circle, and oval. Preferably, the support may have a thickness of 0.5-5.0 mm from the viewpoint of the feeling in use.

The support-equipped pack cosmetics can be produced by extendedly attaching the gel composition heated at 75-85° C. to a support composed of polyester material with a length of 30-100 mm, a width of 20-50 mm and a thickness of 0.5-5.0 mm, followed by cooling at 5-25° C. for 6-24 hours.

The present invention will now be described specifically by way of Examples, which are simply used to demonstrate the present invention and not intended to limit the present invention. The compounding amounts in the following Examples and Comparison examples are represented by mass %.

EXAMPLES

Tamarind Seed Polysaccharides Used

Three commercially available tamarind seed polysaccharides shown in Table 1 were used to prepare gel compositions. The tamarind seed polysaccharides 2 and 3 are the same items but from different production lots. The tamarind seed polysaccharides 2 and 3 are purified tamarind seed polysaccharides obtained by purifying powders of normal-grade tamarind seed polysaccharides. Specifically, the tamarind seed polysaccharides were dispersed in water, then heated and dissolved. The resultant solutions were subjected to activated carbon treating, precise filtering, alcohol precipitating, drying, and pulverizing for production.

TABLE 1

Tamarind Seed Polysaccharides Used

| | Trade Name and Manufacturer | Dietary Fiber (mass %) | Protein (mass %) | Ash (mass %) |
|---|---|---|---|---|
| Tamarind Seed Polysaccharide 1 | Commercially Available Item | 87.4 | 2.0 | 3.9 |
| Tamarind Seed Polysaccharide 2 | Item: Nom Coat EP-2 Available from Nisshin Oillio Group, Ltd. | 93.0 | 0.3 | 0.2 |
| Tamarind Seed Polysaccharide 3 | Item: Nom Coat EP-2 Available from Nisshin Oillio Group, Ltd. | 92.1 | 0.6 | 0.9 |

Examples 1-5 and Comparison Examples 1-3

Formula and Production of Gel Compositions and Compositions

In formulae shown in Table 3, all the components other than the component (C) were fed in the stirring vessel and stirred at 25° C. for 30 minutes. Heating was started while stirring, and when the temperature reached 80° C., stirring was further performed for 30 minutes to dissolve various components. Thereafter, the temperature was adjusted at 50° C., and the component (C) was added, followed by mixing for 30 minutes. The resultant solutions were left stationary at 20° C. for 24 hours to produce gel compositions containing salts of ascorbic acid derivatives in Examples 1-6.

Similarly, compositions in Comparison examples 1-3 were produced in formulae shown in Table 5.

[Method of Estimating Variations in Color and Odor and Occurrences of Aggregations of Produced Compositions]

With respect to the gel compositions in Examples 1-6 and the compositions in Comparison examples 1-3, each 100 g were stored in a temperature-regulated chamber at 50° C. for one month to visually decide variations in color and odor and occurrences of aggregations after storage. The estimated results are shown in Tables 4 and 6. Various estimation standards are shown in Table 2.

[Method of Estimating Gel State of Prepared Compositions]

With respect to the gel compositions in Examples 1-6 and the compositions in Comparison examples 1-3, each 50 g were mounted on an open Petri dish and left stationary at room temperature (25° C.) for 24 hours, then gel states were visually determined. The estimated results are shown in Tables 4 and 6. Various estimation standards are shown in Table 2. The estimated results ⊚ and ○ decide the presence of commodity values and those x and xx decide the absence of commodity values.

TABLE 2

Estimation Standards for Various Estimations

| | Variations in Color | Variations in Odor | Occurrences of Aggregations | Gel State |
|---|---|---|---|---|
| ⊚ | No Variation in Color | No Variation in Odor | No Occurrence of Aggregation | — |
| ○ | Slight Variation in Color | Slight Variation in Odor | Extremely Slight Occurrence of Aggregation | Gel State |
| X | Variation in Color | Variation in Odor | Occurrence of Aggregation | Liquid State |
| XX | Extreme Variation in Color | Extreme Variation in Odor | Extreme Occurrence of Aggregation | — |

TABLE 3

Formula of Gel Composition

| | | Examples | | | | | |
|---|---|---|---|---|---|---|---|
| Components | | 1 | 2 | 3 | 4 | 5 | 6 |
| Component (A) | Tamarind Seed Polysaccharide 1 | 3 | — | — | 5 | — | 3 |
| | Tamarind Seed Polysaccharide 2 | — | 3 | — | — | 4 | 4 |
| | Tamarind Seed Polysaccharide 3 | — | — | 5 | — | — | — |
| | Polyvinyl alcohol | — | — | — | — | — | — |
| | Sodium polyacrylate | — | — | — | — | — | — |
| Component (B) | Glycerin | 30 | — | — | 20 | — | 30 |
| | 1,3-butylene glycol | — | 40 | — | — | 30 | — |
| | Propylene glycol | — | — | 25 | — | — | — |
| Component (C) | Magnesium L-ascorbic acid-2-phosphate | 3 | — | — | 3 | — | 3 |
| | Disodium L-ascorbic acid sulfate | — | 3 | — | — | — | — |
| | Sodium L-ascorbic acid-2-phosphate | — | — | 3 | — | 3 | — |
| | Sodium citrate | 1 | 1 | 1 | 1 | 1 | — |
| Component (D) | Purified Water | Rest | Rest | Rest | Rest | Rest | Rest |
| | Total | 100 | 100 | 100 | 100 | 100 | 100 |
| | pH Immediately after Production | 8.5 | 8.3 | 8.0 | 7.7 | 7.8 | 7.3 |

TABLE 4

Estimated Results of Gel Compositions

| | Examples | | | | | |
|---|---|---|---|---|---|---|
| | 1 | 2 | 3 | 4 | 5 | 6 |
| Variation in Color | ○ | ⊚ | ⊚ | ○ | ⊚ | ○ |
| Variation in Odor | ○ | ⊚ | ⊚ | ○ | ⊚ | ○ |
| Occurrence of Aggregation | ○ | ⊚ | ⊚ | ○ | ⊚ | ○ |
| Gelled State | ○ | ○ | ○ | ○ | ○ | ○ |

TABLE 5

Formula of Gel Composition

| | | Comparison examples | | |
|---|---|---|---|---|
| Components | | 1 | 2 | 3 |
| Component (A) | Tamarind Seed Polysaccharide 1 | 3 | — | — |
| | Tamarind Seed Polysaccharide 2 | — | — | — |
| | Tamarind Seed Polysaccharide 3 | — | — | — |
| | Polyvinyl alcohol | — | 10 | — |
| | Sodium polyacrylate | — | — | 7 |
| Component (B) | Glycerin | — | 20 | — |
| | 1,3-butylene glycol | — | — | 30 |
| | Propylene glycol | — | — | — |

TABLE 5-continued

Formula of Gel Composition

|  |  | Comparison examples | | |
| --- | --- | --- | --- | --- |
|  | Components | 1 | 2 | 3 |
| Component (C) | Magnesium L-ascorbic acid-2-phosphate | 3 | 3 | — |
|  | Disodium L-ascorbic acid sulfate | — | — | — |
|  | Sodium L-ascorbic acid-2-phosphate | — | — | 3 |
|  | Sodium citrate | 1 | 1 | 1 |
| Component (D) | Purified Water | Rest | Rest | Rest |
|  | Total | 100 | 100 | 100 |
|  | pH Immediately after Production | 8.3 | 7.9 | 8.7 |

TABLE 6

Estimated Results of Compositions

|  | Comparison examples | | |
| --- | --- | --- | --- |
|  | 1 | 2 | 3 |
| Variation in Color | ○ | XX | X |
| Variation in Odor | ○ | XX | X |
| Occurrence of Aggregation | X | XX | X |
| Gelled State | X | X | X |

As can be found from the results in Tables 4 and 6, the gel compositions of the present invention can form gels even if they contain salts of ascorbic acid derivatives. In this case, the above various estimations found no variation in color and odor, no occurrence of aggregations, and higher storage stability over time. On the other hand, the compositions other than those of the present invention can not form gels. In this case, the above various estimations found lower storage stability over time.

Example 7

Formula and Production of Sheet Type Pack Cosmetic

The components (A), (B), (D), sodium citrate, methyl parapen, and tetrasodium edetate shown in Table 7 were fed in a stirring vessel and propeller-stirred at 80 C.° for 30 minutes for dissolution. Then, polyoxyethylene-cured castor oil, glycerin trioctanoate, and vitamin E acetate were added, followed by propeller stirring at 80 C.° for 60 minutes. Thereafter, the temperature was adjusted at 50 C.° and the component (C) was added. The resultant solution was supplied in a thin container with a length of 30 mm and a width of 50 mm and left stationary at room temperature for 24 hours for cooling and gelling/solidifying. As a result, a sheet type pack cosmetic containing magnesium L-ascorbic acid-2-phosphate was obtained with a length of 30 mm, a width of 50 and a thickness of about 2 mm.

The resultant sheet type pack cosmetic was subjected to the above various estimations, which found no variation in color and odor, no occurrence of aggregations, and higher storage stability over time, as well as improved moisture retentivity,

TABLE 7

(Example 7) Formula of Sheet Type Pack Cosmetic

|  | Components | Compounding Amount (mass %) |
| --- | --- | --- |
| Component (A) | Tamarind seed polysaccharide 1 | 3.0 |
| Component (B) | Glycerin | 30.0 |
| Component (C) | Magnesium L-ascorbic acid-2-phosphate | 3.0 |
|  | Sodium citrate | 1.0 |
|  | Polyoxyethylene-cured castor oil | 0.5 |
|  | Glycerin trioctanoate | 0.02 |
|  | Vitamin E acetate | 0.05 |
|  | Methylparapen | 0.2 |
|  | Tetrasodium edetate | 0.01 |
| Component (D) | Purified Water | Rest |
| Total |  | 100 |

Example 8

Formula and Production of Support-Equipped Pack Cosmetic

The components (A), (B), (D), sodium citrate, sodium hyaluronate, methyl parapen, and disodium edetate shown in Table 8 were fed in a stirring vessel and propeller-stirred at 30 C.° for 10 minutes for dissolution, followed by propeller stirring at 80 C.° for 90 minutes. Thereafter, the temperature was adjusted at 50 C.° and the component (C) was added. The resultant solution was applied with a thickness of about 2 mm over a sheet of polyester nonwoven with a length of 30 mm and a width of 40 mm and left stationary at 10 C.° for 12 hours for cooling and gelling/solidifying. As a result, a support-equipped pack cosmetic containing sodium L-ascorbic acid-2-phosphate was obtained with a length of 30 mm, a width of 40 and a thickness of about 2 mm.

The resultant support-equipped pack cosmetic was subjected to the above various estimations, which found no variation in color and odor, no occurrence of aggregations, and higher storage stability over time, as well as improved moisture retentivity.

TABLE 8

(Example 8) Formula of Support-Equipped Pack Cosmetic

|  | Components | Compounding Amount (mass %) |
| --- | --- | --- |
| Component (A) | Tamarind seed polysaccharide 2 | 3.0 |
| Component (B) | 1,3-butylene glycol | 10.0 |
|  | Glycerin | 20.0 |
| Component (C) | Sodium L-ascorbic acid-2-phosphate | 3.0 |
|  | Sodium citrate | 1.0 |
|  | Sodium hyaluronate | 0.1 |
|  | Methylparapen | 0.2 |
|  | Disodium edetate | 0.05 |
| Component (D) | Purified Water | Rest |
| Total |  | 100 |

Example 9

Formula and Production of Peel-Off Type Pack Cosmetic

The components (A), (B), (D), sodium citrate/methyl parapen, and tetrasodium edetate shown in Table 9 were fed in a stirring vessel and propeller-stirred at 25 C.° for 30 minutes for dissolution, followed by propeller stirring at 80 C.° for 120 minutes. Thereafter, the temperature was adjusted at 50 C.° and the component (C), menthol, and ethanol were added to obtain a pack cosmetic containing magnesium L-ascorbic acid-2-phosphate. It is heated again for use at 40-50 C.° and used as a peel-off type pack cosmetic.

The resultant peel-off type pack cosmetic was subjected to the above various estimations, which found no variation in color and odor, no occurrence of aggregations, and higher storage stability over time, as well as improved moisture retentivity.

TABLE 9

(Example 9) Formula of Peel-off Type Pack Cosmetic

| | Components | Compounding Amount (mass %) |
|---|---|---|
| Component (A) | Tamarind seed polysaccharide 3 | 5.0 |
| Component (B) | Propylene glycol | 10.0 |
| | Glycerin | 10.0 |
| Component (C) | Magnesium L-ascorbic acid-2-phosphate | 3.0 |
| | Sodium citrate | 1.0 |
| | Menthol | 0.1 |
| | Methylparapen | 0.1 |
| | Ethanol | 30.0 |
| | Tetrasodium edetate | 0.01 |
| Component (D) | Purified Water | Rest |
| Total | | 100 |

INDUSTRIAL AVAILABILITY

The gel compositions and pack cosmetics of the present invention containing one or two or more selected from ascorbic acid, a salt of ascorbic acid, an ascorbic acid derivative, and a salt of an ascorbic acid derivative can be used widely in the fields of cosmetics and medicines.

The invention claimed is:

1. A gel composition, which comprises the following components (A)-(D):
    (A) a tamarind seed polysaccharide;
    (B) a polyhydric alcohol;
    (C) at least one or more of ascorbic acid, a salt of ascorbic acid, an ascorbic acid derivative, and a salt of an ascorbic acid derivative; and
    (D) water
    the component (A) consisting of a tamarind seed polysaccharide including not less than 90% by mass of dietary fiber, not more than 1% by mass of protein, and not more than 1% by mass of ash.

2. The gel composition according to claim 1, wherein the content of the component (A) is 1-20% by mass, the content of the component (B) is 3-50% by mass, the content of the component (C) is 0.01-10% by mass, and the content of the component (D) is 20-95.99% by mass.

3. A pack cosmetic comprising the gel composition according to claim 1.

4. The pack cosmetic according to claim 3, which comprises a support.

5. The gel composition according to claim 1, wherein the content of the component (A) is 1-20% by mass, the content of the component (B) is 3-50% by mass, the content of the component (C) is 0.01-10% by mass, and the content of the component (D) is 20-95.99% by mass.

6. A pack cosmetic comprising the gel composition according to claim 2.

7. A pack cosmetic comprising the gel composition according to claim 5.

8. The pack cosmetic according to claim 6, which comprises a support.

9. The pack cosmetic according to claim 7, which comprises a support.

* * * * *